(12) United States Patent
Gumlich et al.

(10) Patent No.: US 8,372,994 B2
(45) Date of Patent: Feb. 12, 2013

(54) C10 ALKANOIC ACID GLYCIDYL ESTERS AND USE THEREOF

(75) Inventors: Kai Gumlich, Mannheim (DE); Roland Merten, Weinheim (DE); Michael Henningsen, Frankenthal (DE); Martin Schaefer, Gruenstadt (DE); Joaquim Henrique Teles, Otterstadt (DE); Bernhard Mohr, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 185 days.

(21) Appl. No.: 12/666,666

(22) PCT Filed: Jun. 24, 2008

(86) PCT No.: PCT/EP2008/058036
§ 371 (c)(1),
(2), (4) Date: Dec. 24, 2009

(87) PCT Pub. No.: WO2009/000839
PCT Pub. Date: Dec. 31, 2008

(65) Prior Publication Data
US 2010/0180802 A1    Jul. 22, 2010

(30) Foreign Application Priority Data
Jun. 28, 2007 (EP) .................................. 07111275

(51) Int. Cl.
*C07D 303/42* (2006.01)

(52) U.S. Cl. ........ 549/557; 549/200; 549/512; 549/555; 549/556; 549/561; 549/562; 525/386; 524/317; 528/421; 106/505

(58) Field of Classification Search .................. 549/200, 549/512, 555, 556, 557, 561, 562; 525/386; 524/317; 528/421; 106/505
See application file for complete search history.

(56) References Cited

U.S. PATENT DOCUMENTS

| | | | | |
|---|---|---|---|---|
| 3,178,454 | A | * | 4/1965 | Kloos et al. .................. 549/515 |
| 5,036,154 | A | | 7/1991 | Au |
| 6,433,217 | B1 | | 8/2002 | Rosenbrand et al. |
| 6,946,502 | B1 | * | 9/2005 | Lahtinen et al. ............. 523/412 |

FOREIGN PATENT DOCUMENTS

| | | |
|---|---|---|
| DE | 2 107 084 | 9/1972 |
| DE | 24 46 944 | 4/1976 |
| DE | 102 39 134 | 1/2003 |
| DE | 10239134 | * 1/2003 |
| EP | 0 697 018 | 2/1996 |
| EP | 1 042 402 | 10/2000 |
| EP | 1 115 714 | 7/2001 |
| WO | 00 44836 | 8/2000 |

OTHER PUBLICATIONS

Translation of DE 10239134.*
Bukowska Agnieszka, et al., "Synthesis of glycidyl esters", Journal of Chemical Technology and Biotechnology, vol. 74, pp. 1145-1148, XP002494101, (1999).
U.S. Appl. No. 13/142,968, filed Jun. 30, 2011, Teles, et al.

* cited by examiner

*Primary Examiner* — Robert C Boyle
(74) *Attorney, Agent, or Firm* — Oblon, Spivak, McClelland, Maier & Neustadt, L.L.P.

(57) ABSTRACT

Glycidyl 2-propylheptanoate, glycidyl 4-methyl-2-propylhexanoate or a mixture of these (referred to collectively for short as glycidyl ester).

18 Claims, No Drawings

C10 ALKANOIC ACID GLYCIDYL ESTERS AND USE THEREOF

The invention relates to glycidyl 2-propylheptanoate, glycidyl 4-methyl-2-propylhexanoate or a mixture of these (referred to collectively for short as glycidyl ester).

The physical and chemical properties of glycidyl esters endow them with diverse possibilities for use. They are used, for example, as reactive diluents for polyacrylates, polyesters or epoxide systems, possess suitability as dispersing assistants, for pigments, for example, or are employed as intermediates in syntheses, more particularly for the modifying of oligomers and polymers. Known examples include, more particularly, branched C 10 alkanoic acid glycidyl esters, examples being glycidyl esters of Versatic acid, like those available under the trade name Cardura® E 10 from Shell, or glycidyl esters of neodecanoic acid, of the kind available under the name Glydexx® from Exxon.

Agnieszka Bukowska et al., J. Chem. Technol Biotechnol 74 (1999) 1145-1148 describe the preparation of glycidyl esters by reaction of the corresponding carboxylic acids with epichlorohydrin in the presence of chromium(II) salts and subsequent ring closure to form the glycidyl ester, using acetonitrile and potassium carbonate. The product is purified by distillation.

U.S. Pat. No. 6,433,217 discloses the preparation of glycidyl esters branched on the alpha C atom, more particularly esters of Versatic acid, by reaction of the carboxylic acid with epichlorohydrin in the presence of a catalyst, subsequent addition of an alkali metal hydroxide, and workup by distillation.

Uses of the glycidyl esters as reactive diluents or dispersing assistants, for pigments, for example, or for modifying polymers by means of polymer-analogous reaction, are known within the market. EP 1 042 402, for example, describes their use in coating compositions.

There is a need for alternative glycidyl esters having excellent performance properties and being, as far as possible, simple and inexpensive to produce.

Accordingly the above-defined glycidyl esters and their use have been found. Also found has been a process for preparing them.

The glycidyl esters and their preparation

The glycidyl esters of the invention are glycidyl 2-propylheptanoate of the formula

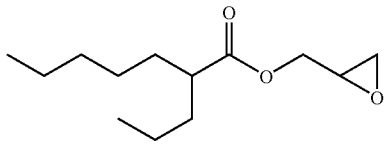 [SMILES: CCCCCC(CCC)C(=O)OCC1CO1]

or glycidyl 4-methyl-2-propylhexanoate of the formula

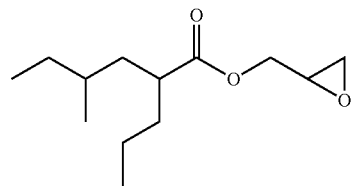 [SMILES: CCCC(CC(C)CC)C(=O)OCC1CO1]

or a mixture of the two.

The glycidyl esters of the invention are liquid at 1 bar and 21° C.

Glycidyl 2-propylheptanoate, glycidyl 4-methyl-2-propylhexanoate or a mixture of the two is easily obtained by dimerization of pentenes and subsequent oxidation. Dimerization of pentenes and subsequent oxidation is described in DE-A 102 39 134.

Generally speaking, however, there is no need for this, since both carboxylic acids and both glycidyl esters derived from them are suitable for the further uses in the context of this invention. Preferably, however, the mixture is oxidized to the corresponding carboxylic acid mixture without separation of the alkenes. In the course of the dimerization and subsequent oxidation there may be further byproducts produced, examples being formic esters, such as 1-propylhexyl formate or 3-methyl-1-propyl-pentyl formate, mixtures of nonanol or 6-methyloctan-4-ol and formic acid; separating off these byproducts prior to preparation and further use of the glycidyl esters is unnecessary.

The amount of these byproducts, however, is preferably less than 20 parts by weight, more particularly less than 10 parts by weight, with particular preference less than 5 parts by weight, per 100 parts by weight of 2-propylheptanoic acid, 4-methyl-2-propylhexanoic acid or their weight sum.

With particular preference the glycidyl ester of the invention is a mixture of glycidyl 2-propylheptanoate and glycidyl 4-methyl-2-propylhexanoate.

With particular preference the fraction of the two compounds is
1% to 99% by weight of glycidyl 2-propylheptanoate and
1% to 99% by weight of glycidyl 4-methyl-2-propylhexanoate,
the percentage being based on the sum of the two.

With particular preference the mixture is composed of
10% to 90%, more particularly 20% to 80% by weight of glycidyl 2-propylheptanoate and
10% to 90%, more particularly 20% to 80% by weight of glycidyl 4-methyl-2-propylhexanoate.

Examples of processes suitable for preparing the glycidyl esters of the invention include the following:

The process DE-A 2107084 describes processes for transesterifying carboxylic acid methyl ester with glycidyl acetate or glycidyl propionate, using sodium methoxide or ammonium hydroxides as catalysts; the resulting methyl acetate is removed by distillation.

Reaction of carboxylic acid with a boiling mixture of epichlorohydrin (2.5 times molar excess) and sodium carbonate (0.5 mol with respect to the acid). In accordance with DE-A 2446944. Water of reaction and epichlorohydrin separate in the water separator. Epichlorohydrin is recycled. When all of the water has been removed, triethylbenzylammonium chloride is added, followed by stirring at 110-115° C. and, following filtration (NaCl), workup by distillation.

Another process is the esterification of carboxylic acids with glycidol using carbodiimides (e.g., DCC) as acylating reagents and pyridines (e.g., DMAP) as catalysts, in accordance with EP-A 0697018. Urea is isolated by filtration, and the catalyst is removed using an acidic ion exchange resin. Residual carbodiimide is destroyed using 50% strength aqueous acetic acid. Solvent is removed under reduced pressure. Crude product is taken up in organic solvent, and residual urea is isolated by crystallization with cooling. Solvent is distilled off under reduced pressure. Product remains as residue.

In accordance with U.S. Pat. No. 5,036,154 the reaction takes place by means of sodium tungstate-catalyzed epoxidation of allyl esters with $H_2O_2$ in 70% form. This is a 2-phase reaction (water/toluene) using trioctylammonium chloride as a phase transfer catalyst (PTC).

EP 1115714 describes the reaction of neodecanoic acid with an approximately 4-fold molar excess of epichlorohydrin in the presence of isopropanol (water-miscible alcohol), water, and NaOH.

Neodecanoic acid, epichlorohydrin, and the solvents are introduced initially, followed by metered addition of 50% strength NaOH at 56° C. Temperature is raised to 84° C., then cooled to 50° C. After the lower phase has been separated off, 24% strength NaOH is metered in at 50° C. Phase separation takes place after 40 minutes. The organic phase is concentrated until the final conditions of 100 mbar and 110° C. are reached. Excess epichlorohydrin is removed by steam distillation. Then 50% strength NaOH is added at 55° C. The reaction time is followed by two-fold extraction with water; organic phase is stripped with steam and dried under reduced pressure (120° C., 40 mbar).

According to WO 00/44836, 1 mol of 2-ethylhexanoic acid and 2 mol of NaOH are used to prepare the Na salt of the acid in toluene. Water formed is distilled off azeotropically using toluene. 3 mol of epichlorohydrin are slowly added at 50° C. The mixture is heated at reflux. After the end of reaction the epichlorohydrin is distilled off under. The product is distilled under reduced pressure.

A preferred process for preparing the glycidyl esters of the invention is characterized by the following steps a) to c):

a) reacting 2-propylheptanoic acid, 4-methyl-2-propylhexanoic acid or a mixture thereof with epichlorohydrin in the presence of a chromium salt,
b) reacting the resulting hydroxyl compound in the presence of an alkali metal hydroxide or alkaline earth metal hydroxide to give the glycidyl ester, and
c) then, if appropriate, working up the resulting mixture extractively.

In step a) of the process it is preferred to use epichlorohydrin in amounts of 0.9 to 2 mol, more preferably in amounts of 1 to 1.5 mol, per mole of alkanecarboxylic acid.

The chromium salt may be any desired salt of chromium (II) or chromium(III), with particular suitability being possessed by salts of carboxylic acids (alkanoate), e.g., chromium(II) acetate or chromium(II) ethylhexanoate or chromium(II) hydroxides or else mixed anions (hydroxide and alkanoate).

The chromium salt is used preferably in amounts of 0.0001 to 0.01 mol, more preferably of 0.0005 to 0.005 mol, per mole of alkanecarboxylic acid.

The reaction in step a) of the process is carried out preferably under atmospheric pressure (1 bar) and at a temperature of 30 to 100° C., preferably 60 to 90° C. A solvent can be used in the reaction; generally speaking, however, no solvent is needed.

The reaction in step a) of the process is preferably monitored by gas chromatography; preferably there is complete conversion of the alkanecarboxylic acid to the hydroxyl compound.

Step b) of the process preferably follows directly on from step a) of the process, without workup after the end of reaction in step a) of the process.

The alkali metal hydroxide or alkaline earth metal hydroxide may be any desired hydroxide, preferably an alkali metal hydroxide such as NaOH or KOH.

The alkali metal hydroxide or alkaline earth metal hydroxide is used preferably in amounts of 1 to 2 mol per mole of the hydroxyl compound obtained in step a) of the process; this molar amount preferably corresponds to the amount of alkanecarboxylic acid used since reaction in step a) of the process is preferably complete.

The reaction in step b) of the process is preferably likewise carried out under atmospheric pressure (1 bar) and at a temperature of 30 to 100° C., preferably 30 to 80° C.

The rate of dropwise addition is preferably selected such that the temperature remains within the chosen range, with preferably stirring for a while—two hours, for example—after the end of the addition of the alkali metal or alkaline earth metal hydroxide. The reaction can preferably be monitored by gas chromatography.

This is followed preferably by extractive workup of the mixture obtained according to step b) of the process. Particular preference is given to extractive workup with water. The aqueous phase and organic phase obtained are separated and the organic phase is dried, preferably by addition of a dryer such as sodium sulfate.

The glycidyl ester can be obtained in high purity and yield in the process of the invention. With the process of the invention, moreover, a very simple and cost-effective method is provided for the synthesis of the alkanecarboxylic acids.

The Use

The glycidyl esters of the invention are suitable, for example, as reactive diluents. Reactive diluents, when added to a composition, produce a reduction in the viscosity; when the composition subsequently cures, they are bound to components of the composition which are able to react with the reactive diluents, thereby becoming part of the resulting product—a coating or a molding, for example.

When the glycidyl esters are used as reactive diluents the composition ought to comprise compounds which are reactive with the glycidyl group—for example, the compounds ought to comprise carboxylic acid groups, hydroxyl groups or primary or secondary amino groups. When the composition is cured, by an increase in temperature or by irradiation with high-energy light, for example, the corresponding attachment then occurs.

The compositions which comprise the glycidyl ester ought preferably to be liquid at 21° C. and 1 bar, and curable. The compositions in question, more particularly, are thermally curable coating compositions.

The compositions comprise preferably at least 0.1% by weight, more preferably at least 0.5%, very preferably at least 1% or else at least 3% by weight, or, in one particular embodiment, at least 5% by weight, of the glycidyl ester of the invention; generally speaking, however, the amount of the glycidyl ester does not exceed 50%, preferably not 30%, or not 20% by weight. These percentages are based on all of the constituents of the composition bar water and organic solvents.

Suitable compounds reactive with the glycidyl group include low molecular mass compounds, but also oligomeric or polymeric compounds.

Polymeric compounds include, for example, polymers obtainable by free-radical addition polymerization, such as polyacrylates or polyvinyl esters, polyesters or polyurethanes, which contain groups reactive with the glycidyl ester, examples being carboxylic acid groups, hydroxyl groups or amino groups.

Suitable compositions comprise, in particular, customary epoxides, which in the text below is a term used to refer to compounds having at least one epoxide group, apart from the glycidyl esters of the invention. The glycidyl ester likewise comprises epoxy groups. The epoxides and the glycidyl ester can then cure in the same way; by addition of an amine curative or an anhydride curative (hardener), for example.

With particular preference the curable composition comprises epoxides having 2 to 6, very preferably having 2 to 4, and in particular having 2 epoxy groups.

The epoxy groups of the epoxides are, more particularly, glycidyl ether groups, of the kind formed in the reaction of alcohol groups with epichlorohydrin.

The epoxides may be low molecular mass compounds, which in general have an average molar weight, Mn, of less than 1000 g/mol, or compounds of higher molecular mass (polymers). They may be aliphatic compounds, including cycloaliphatic compounds, or compounds containing aromatic groups.

In particular the epoxides are compounds having two aromatic or aliphatic 6-membered rings, or oligomers thereof.

Of significance in the art are epoxides which are obtainable by reaction of epichlorohydrin with compounds that have at least two reactive H atoms, more particularly with polyols.

Of particular significance in the art are epoxides which are obtainable by reaction of epichlorohydrin with compounds which contain at least two, preferably two hydroxyl groups and two aromatic or aliphatic 6-membered rings; such compounds include, in particular, bisphenol A and bisphenol F, and also hydrogenated bisphenol A and bisphenol F.

Also suitable are reaction products of epichlorohydrin with other phenols, such as with cresols or phenol-aldehyde adducts, such as phenol-formaldehyde resins, more particularly novolaks.

Also suitable, of course, are epoxides which do not derive their epoxy groups from epichlorohydrin. Suitable examples include epoxides which comprise epoxy groups by virtue of reaction with glycidyl (meth)acrylate, e.g., free-radical copolymerization with glycidyl (meth)acrylate. Mention may also be made in this context of ERL-4221 from Dow (CAS number 2386-87-0):

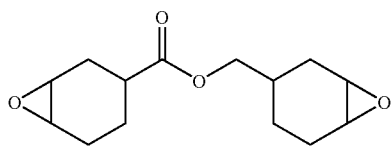 [SMILES: O=C(OCC1CCC2OC2C1)C1CCC2OC2C1]

Epoxides that are suitable for the use of the compositions are more particularly those epoxides which are liquid at processing temperatures of 20 to 100° C., more preferably at 20 to 40° C., very preferably at 20° C. Solid epoxides can be dissolved in a suitable solvent or else, preferably, in the glycidyl ester of the invention as reactive diluent.

In the case of the epoxide compounds the composition preferably further comprises at least one curative or hardener.

Those suitable include anhydride crosslinkers, such as phthalic anhydride, trimellitic anhydride, benzophenonetetracarboxylic dianhydride, tetrahydrophthalic anhydride, hexahydrophthalic anhydride, 4-methyltetrahydrophthalic anhydride, 3-methyltetrahydrophthalic anhydride, 4-methylhexahydrophthalic anhydride or 3-methylhexahydrophthalic anhydride, for example.

Also suitable, in particular, are amines; known amine crosslinkers are, more particularly, aliphatic polyamines such as diethylenetriamine, triethylenetetramine or amines based on propylene oxide and ammonia (polyether amines).

Depending on the reactivity of the crosslinkers, they may already be added at an early stage to the composition (one-component or 1 K system), or not until shortly before use (two-component or 2 K system).

Preferred compositions have an epoxide compound content of at least 30%, preferably at least 50%, very preferably at least 70% by weight (not including any solvents used).

In one preferred embodiment the composition comprises inert solvents, if at all, only in minor amounts (less than 20 parts by weight, more particularly less than 10 or less than 5 parts by weight per 100 parts by weight of epoxide compound), and with particular preference comprises no solvent (100% system).

The compositions which comprise epoxides are suitable, for example, as coating or impregnating materials, as an adhesive, as composite material, for producing shaped articles, or as casting compounds for embedding, attaching or solidifying shaped articles. This and the remarks below apply both to the 1 K and to the 2 K systems.

Examples of coating materials include paints and varnishes. Using the compositions of the invention (1 K or 2 K) it is possible in particular to obtain scratch-resistant protective coatings on any desired substrates, made of metal, plastic or wood-based materials, for example. The compositions also suitable as insulating coatings in electronic applications, such as an insulating coating for wires and cables, for example. Mention may also be made of their use for producing photoresists. They are also suitable, in particular, as repair coating material, including in connection, for example, with the repair of pipes without their disassembly (cure in place pipe (CIPP) rehabilitation). They are additionally suitable for the sealing of floors.

Adhesives include 1 K or 2 K structural adhesives. Structural adhesives serve to connect shaped parts permanently to one another. The shaped parts may be of any desired material: suitable materials include plastic, metal, wood, leather, ceramic, etc. Adhesives in question may also be hot melt adhesives, which are fluid and can be processed only at a relatively high temperature. They may also be flooring adhesives. The compositions are also suitable as adhesives for producing printed circuit boards (electronic circuits), not least by the SMT method (surface mounted technology).

In composites, different materials, such as plastics and reinforcing materials (fibers, carbon fibers), for example, are joined to one another.

The compositions are suitable, for example, for producing preimpregnated fibers, e.g., prepregs, and for their further processing to composites.

Production methods for composites include the curing of preimpregnated fibers or woven fiber fabrics (e.g., prepregs) after storage, or else extrusion, pultrusion, winding, and resin transfer molding (RTM), called resin infusion technologies (RI).

The fibers can be impregnated with the composition of the invention, in particular, and thereafter cured at a relatively high temperature. In the course of impregnation and any subsequent storage period, curing does not begin or is only minimal.

As casting compounds for embedding, attaching or solidifying shaped articles, the compositions are employed, for example, in electronics applications. They are suitable as flip-chip underfill or as electrical casting resins for potting, casting, and (glob-top) encapsulation.

The coatings, shaped articles or other products produced using the compositions are notable for very good performance properties, more particularly for high strength, high scratch resistance, good chemical resistance, and good hardness and elasticity.

The glycidyl esters of the invention are additionally suitable as dispersing or emulsifying assistants.

Contemplated more particularly is their use as dispersing assistants for pigments. Pigment compositions, such as pigment pastes or pigment dispersions, comprise preferably 0.1 to 30 parts by weight, more preferably 0.05 to 20 parts by weight, of the glycidyl ester, based on 100 parts by weight of pigment.

The glycidyl ester is suitable, moreover, for the chemical modification of both low molecular mass compounds and polymeric compounds. An essential prerequisite is that the compound comprises a functional group which is reactive with the glycidyl group of the glycidyl ester. Suitable groups, as already set out above, are hydroxyl groups, primary or secondary amino groups, and carboxyl groups. The low molecular mass or polymeric compounds thus modified are suitable, for example, as binders, especially as binders in coating systems. These may be water-free and solvent-free binders, including, for example, radiation-curable binders. Preferred binders are polyacrylate resins of which more than 40% by weight, in particular more than 60% by weight, is composed of $C_1$-$C_{20}$ alkyl (meth)acrylates.

Glycidyl ester is suitable more particularly for modifying polymers obtainable by free-radical addition polymerization, polyacrylates for example, polycondensates, polyesters for example, or polyadducts, polyurethanes for example.

Suitable polymers obtainable by free-radical addition polymerization of unsaturated compounds (monomers) are composed preferably of at least 40%, more preferably of at least 60%, with particular preference of at least 80% by weight of what are called principal monomers.

The principal monomers are selected from $C_1$-$C_{20}$ alkyl (meth)acrylates, vinyl esters of carboxylic acids comprising up to 20 C atoms, vinylaromatics having up to 20 C atoms, ethylenically unsaturated nitriles, vinyl halides, vinyl ethers of alcohols comprising 1 to 10 C atoms, aliphatic hydrocarbons having 2 to 8 C atoms and one or two double bonds, or mixtures of these monomers.

Examples include (meth)acrylic acid alkyl esters with a $C_1$-$C_{10}$ alkyl radical, such as methyl methacrylate, methyl acrylate, n-butyl acrylate, and 2-ethylhexyl acrylate.

Also suitable in particular are mixtures of the (meth)acrylic acid alkyl esters.

Vinyl esters of carboxylic acids having 1 to 20 C atoms are for example vinyl laurate, vinyl stearate, vinyl propionate, Versatic acid vinyl esters, and vinyl acetate.

Suitable vinylaromatic compounds include vinyltoluene, α- and p-methylstyrene, α-butylstyrene, 4-n-butylstyrene, 4-n-decylstyrene and, preferably, styrene. Examples of nitriles are acrylonitrile and methacrylonitrile.

The vinyl halides are chlorine-, fluorine- or bromine-substituted ethylenically unsaturated compounds, preferably vinyl chloride and vinylidene chloride.

Examples of vinyl ethers include vinyl methyl ether and vinyl isobutyl ether. Preference is given to vinyl ethers of alcohols comprising 1 to 4 C atoms.

Hydrocarbons having 2 to 8 C atoms and one or two olefinic double bonds include ethylene, propylene, butadiene, isoprene, and chloroprene.

Preferred principal monomers are $C_1$-$C_{10}$ alkyl (meth)acrylates and mixtures of the alkyl (meth)acrylates with vinylaromatics, more particularly styrene (polyacrylates).

Besides the principal monomers the polymer preferably comprises further monomers, examples being monomers having a carboxylic acid group, hydroxyl group or amino group. The presence of these functional groups enables the attachment of the glycidyl esters of the invention. Examples of such monomers include acrylic acid, methacrylic acid, maleic acid, itaconic acid, C1 to C10 hydroxyl acrylates, acrylamide or methacrylamide.

Compositions which comprise glycidyl 2-propylheptanoate, glycidyl 4-methyl-2-propylhexanoate or a mixture thereof as reactive diluent have in particular a relatively low viscosity. Accordingly binders modified with these glycidyl esters also have a relatively low viscosity.

Possibilities afforded by a relatively low viscosity include, in particular, a higher solids content, or a higher pigments content. The binders, including polyacrylate resins in particular, have good substrate wetting and wetting of pigments.

The compositions and binders have good performance properties, such as hardness, flexibility, and gloss.

EXAMPLES

Comparative Example 1

Synthesis of Glycidyl 2-ethylhexanoate in Analogy to the Literature Instructions (J. Chem. Technol. Biotechnol. 74 (1999), 1145-48)

The acid (72.0 g) was charged together with chromium(III) acetate hydroxide (0.10 g) to a flask (250 ml 4-necked flask with condenser, dropping funnel, and magnetic stirrer), this initial charge was heated, and, when 80° C. had been reached, the epichlorohydrin (46.3 g) was added dropwise over the course of an hour (slightly exothermic). When stirring had been carried out at temperature overnight, the mixture was transferred, with addition of acetonitrile (100 ml) with dry K2CO3 (100 g), to a 500 ml flask, and was stirred at reflux (=82° C.) for 2 working days. After cooling and filtration, the mixture was concentrated on a rotary evaporator and the residue was extracted by shaking 3× with ice/water. Yield: 65%

Comparative Example 2

Synthesis of Glycidyl 2-ethylhexanoate with Cr(II) Ethylhexanoate as Catalyst

The acid (72.0 g) was charged together with chromium(II) ethyl hexanoate (0.24 g) to a flask (250 ml 4-necked flask with condenser, dropping funnel, and magnetic stirrer), this initial charge was heated, and, when 80° C. had been reached, the epichlorohydrin (46.3 g) was added dropwise over the course of an hour (slightly exothermic). After a subsequent stirring time of 6 hours, the mixture was transferred, after addition of acetonitrile (100 ml) with dry K2CO3 (69.1 g), to a 500 ml flask, and was stirred intensively at reflux (=82° C.). The course of the reaction was monitored by GC. Since the reaction of chloride to epoxide came to a standstill, a further 20 g of K2CO3 were added and stirring was continued for 2 working days. After the salt residues had been separated off (glass suction filter), the discharge from the reaction was concentrated on a rotary evaporator and the residue was distilled under reduced pressure (1.5 mbar).

| Fr. 1 b.p. = 90° C. (1.5 mbar) | 95.5 area % | glycidyl 2-ethylhexanoate |
| --- | --- | --- |
| | 1.0 area % | isomer |
| | 0.95 area % | diol compound from epoxide |
| Fr. 2 b.p. = 90° C. (1.5 mbar) | 96.0 area % | glycidyl 2-ethylhexanoate |
| | 1.0 area % | isomer |
| | 0.86 area % | diol compound from epoxide |
| Fr. 3 b.p. = 90° C. (1.5 mbar) | 91.0 area % | glycidyl 2-ethylhexanoate |
| | 1.7 area % | isomer |

-continued

| | | |
|---|---|---|
| Liquid phase | 3.0 area % | diol compound from epoxide |
| | 19.5 area % | glycidyl 2-ethylhexanoate |
| | 3.5 area % | isomer |
| | 24.0 area % | diol compound from epoxide |
| | 20 and 22% | 2 unknown compounds |
| Fr. 1 | 41.1 g | |
| Fr. 2 | 20.1 g | |
| Fr. 3 | 2.8 g | |
| Liquid phase | 21.8 g | |
| Total: | 95.8 g | theoretical final mass: 100.0 g |
| Yield from fraction 1 + 2: | 58.6% | |

Preparation Example 1

Synthesis of Glycidyl 2-propylheptanoate with Distillative Workup

The acid (86 g) was charged together with the chromium (III) acetate hydroxide (0.10 g) to a flask (500 ml 4-necked flask with condenser, intensive stirrer, and dropping funnel), this initial charge was heated, and, when 80° C. had been reached, the epichlorohydrin (46.3) was added dropwise over the course of an hour (slightly exothermic). After a subsequent stirring time of 6 hours, and after addition of acetonitrile (100 ml) with dry K2CO3 (100 g), the mixture is stirred at reflux (=82° C.). The course of the reaction was monitored by GC.
Yield after distillation: 61%

Preparation Example 2

Synthesis of Glycidyl 2-propylheptanoate with Extractive Workup

The acid (688 g) was charged together with the chromium salt (0.8 g) to a reactor (3 l jacketed reactor with impeller stirrer and also with 2 gas condensers in series. The jacket of the reactor and the gas cooler are each equipped with heating and/or cooling thermostats.), the initial charge was heated, and, when 80° C. had been reached, the epichlorohydrin (398 g) was added dropwise over 2 hours, followed by stirring for 24 hours. After GC checking, the fully converted intermediate was admixed with aqueous sodium hydroxide solution (480 g, 50% strength). With the aid of the rate of dropwise addition, the temperature was held at 55° C. during this stage. After a subsequent stirring time of 2 hours, the batch was diluted with 3 l of water and stirred at temperature for 10 minutes, and, after a half-hour time for settlement, the two phases were separated. The upper, organic phase was dried twice with sodium sulfate. Determination of water after the drying agent had been removed by filtration gave 0.4% of water, whereupon the product was dried further under a stream of nitrogen with a bath temperature of 55° C. Residual epichlorohydrin was removed by stripping with $N_2$ at 115° C. for 3 hours.
Yield: 66%

Use Example

Preparation of an Acrylate Resin Modified with Glycidyl 2-propylheptanoate

Into a laboratory reactor with indirect heating (heat transfer oil) or regulable, electric resistance heating; product temperature monitoring; inert gas introduction, steplessly regulable stirrer, two feed containers, and reflux condenser, 298 g of a solvent comprising alkyl aromatics having a boiling range of 158-172° C. and 241.6 g of glycidyl 2-propylheptanoate are weighed and this initial charge is heated with stirring, during which inert gas (nitrogen) is passed through it.

Weighed in separately are 201.3 g of styrene, 145.0 g of methyl methacrylate, 147.4 g of 2-hydroxyethyl methacrylate and 70.1 g of acrylic acid, which are premixed and fed to the first feed container (monomer mixture). The second feed container receives a mixture of 40.3 g of the stated aromatic solvent and 40.3 g of tert-butyl perethylhexanoate (initiator solution). The contents of the laboratory reactor are heated to 140° C. and stirred continuously. Then a uniform feed of the initiator solution is started, over a time of 4.75 hours. A quarter of an hour after the beginning of the initiator feed, the uniform feed of the monomer mixture is commenced. Throughout the feed times, the temperature is held with maximum precision at 140° C. After the end of the monomer feed, the initiator feed is continued for half an hour more. After the end of the initiator feed, the determination of the solids (EN ISO 3251, about 1.0 g, 15' 180° C.) is commenced. The temperature is held at 140° C. until the solids is above 71% and no longer undergoes any significant change, but at least for three measurements. Then the batch is cooled and the acrylate resin solution produced is discharged. It is adjusted to a solids (60' 130° C.) of 70.0±1.0% with 16.1 g of the stated aromatic solvent.

The resulting acrylate resin has an acid number of 6.8 mg KOH/g, an OH number of 148 mg KOH/g, and a viscosity of 26.4 Pa·s (23° C.).

The acrylate resin obtained is particularly suitable for producing two-component coating materials which comprise as their curing agent polyisocyanate adducts, an example being the isocyanurate trimer of hexamethylene diisocyanate. They also exhibit good properties in other coating systems, however.

The 2-propylheptanoic acid-modified acrylate resin described here displays advantages relative to customary acrylate resins comprising OH groups. The coating materials obtained therefrom have significantly lower viscosities as compared with acrylate resins produced under the same reaction conditions but without glycidyl ester modification in the manner described, and permit a comparably higher application solids, which means a lower VOC. The acrylate resins thus modified produce, for the coating systems, better pigment wetting, better sprayability, better substrate wetting, better gloss and fullness of the applied films. The OH groups of different reactivity that result from the modification produce advantages for crosslinking in respect of the extension of the molecular networks in the coating film.

In comparison to the existing products based on the glycidyl ester of 2,2,3,5-tetramethylhexanoic acid, the binders based on the glycidyl ester of 2-propylheptanoic acid exhibit lower solution viscosities, which allow the formulation of coating systems with 5-10% higher application solids (a particular current requirement of the coatings industry for the purpose of compliance with VOC regulations), better application properties (flow), and better flexibility. The hardness values of the coatings, achieved by way of comparison, meet the requirements set.

The invention claimed is:

1. A glycidyl ester composition comprising a mixture of glycidyl 2-propylheptanoate and glycidyl 4-methyl-2-propylhexanoate,
    wherein a content of the glycidyl 2-propylheptanoate is from 1% to 99% by weight, based on a weight sum of glycidyl 2-propylheptanoate and glycidyl 4-methyl-2-propylhexanoate, and a content of the glycidyl 4-methyl-2-propylhexanoate is from 1% to 99% by weight, based on the weight sum of glycidyl 2-propylheptanoate and glycidyl 4-methyl-2-propylhexanoate.

2. The glycidyl ester composition of claim 1,
wherein the content of the glycidyl 2-propylheptanoate is from 10% to 90% by weight, based on the weight sum of glycidyl 2-propylheptanoate and glycidyl 4-methyl-2-propylhexanoate, and
the content of the glycidyl 4-methyl-2-propylhexanoate is from 10% to 90% by weight, based on the weight sum of glycidyl 2-propylheptanoate and glycidyl 4-methyl-2-propylhexanoate.

3. The glycidyl ester composition of claim 1,
wherein the content of the glycidyl 2-propylheptanoate is from 20% to 80% by weight, based on the weight sum of glycidyl 2-propylheptanoate and glycidyl 4-methyl-2-propylhexanoate, and
the content of the glycidyl 4-methyl-2-propylhexanoate is from 20% to 80% by weight, based on the weight sum of glycidyl 2-propylheptanoate and glycidyl 4-methyl-2-propylhexanoate.

4. A process for preparing the glycidyl ester composition of claim 1, the process comprising:
a) reacting 2-propylheptanoic acid and 4-methyl-2-propylhexanoic acid with epichlorohydrin in the presence of a chromium salt, and
b) reacting the resulting hydroxyl compound in the presence of an alkali metal hydroxide or alkaline earth metal hydroxide to give the glycidyl ester.

5. The claim 4, further comprising working up the resulting mixture extractively.

6. A curable composition, liquid at 21° C. and 1 bar, comprising the glycidyl ester composition of claim 1.

7. The composition according to claim 6, comprising at least 0.1% by weight of the glycidyl ester composition, based on all constituents of the composition bar water and organic solvents.

8. A pigment preparation comprising from 0.05 to 20 parts by weight of the glycidyl ester composition according to claim 1, based on 100 parts by weight of pigment.

9. A polymer obtained by free-radical addition polymerization, a polycondensate, or a polyadduct, which has been modified by reaction with the glycidyl ester composition of claim 1.

10. A method of diluting comprising adding the glycidyl ester composition of claim 1 to a composition in need thereof.

11. A method of diluting a composition comprising an epoxide compound, the method comprising adding the glycidyl ester composition of claim 1 to a composition in need thereof.

12. A method of dispersing comprising adding the glycidyl ester composition of claim 1 to a composition in need thereof.

13. A method of emulsifying comprising adding the glycidyl ester composition of claim 1 to a composition in need thereof.

14. A method of dispensing a pigment, the method comprising adding the glycidyl ester composition of claim 1 to a composition in need thereof.

15. A method of modifying a polymer, the method comprising adding the glycidyl ester composition of claim 1 to the polymer.

16. The method of claim 15 wherein the polymer is obtained by free radical polymerization.

17. The method of claim 15 wherein the polymer is a polycondensate.

18. The method of claim 15 wherein the polymer is polyadduct.

* * * * *